US011246760B2

(12) United States Patent
Ahsani Ghahreman et al.

(10) Patent No.: US 11,246,760 B2
(45) Date of Patent: Feb. 15, 2022

(54) SELF-ADHESIVE MEMBER

(71) Applicant: Mölnlycke Health Care AB, Gothenburg (SE)

(72) Inventors: Sami Ahsani Ghahreman, Gothenburg (SE); Dennis Hansson, Gunnilse (SE)

(73) Assignee: MÖLNLYCKE HEALTH CARE AB, Gothenburg (SE)

( * ) Notice: Subject to any disclaimer, the term of this patent is extended or adjusted under 35 U.S.C. 154(b) by 620 days.

(21) Appl. No.: 15/505,983

(22) PCT Filed: Jun. 26, 2015

(86) PCT No.: PCT/EP2015/064544
§ 371 (c)(1),
(2) Date: Feb. 23, 2017

(87) PCT Pub. No.: WO2016/030047
PCT Pub. Date: Mar. 3, 2016

(65) Prior Publication Data
US 2017/0258640 A1    Sep. 14, 2017

(30) Foreign Application Priority Data

Aug. 28, 2014    (EP) .................................... 14182641

(51) Int. Cl.
*A61F 13/02*    (2006.01)
*A61F 13/00*    (2006.01)
(52) U.S. Cl.
CPC ...... *A61F 13/023* (2013.01); *A61F 13/00038* (2013.01); *A61F 13/02* (2013.01);
(Continued)
(58) Field of Classification Search
CPC .... A61F 13/023; A61F 13/02; A61F 13/0226; A61F 2013/00582; A61F 13/00038;
(Continued)

(56) References Cited

U.S. PATENT DOCUMENTS 2,096,564 A    10/1937    Scholl
7,888,546 B2 *    2/2011    Marcoux ............... A61F 13/023
602/52

(Continued)

FOREIGN PATENT DOCUMENTS

DE    102011002268 A1    10/2012
GB    821959    10/1959

(Continued)

OTHER PUBLICATIONS

International Search Report and Written Opinion dated Jul. 8, 2016 by the International Searching Authority for International Patent Application No. PCT/EP2016/058691, which was filed on Apr. 20, 2016 and published as WO 2016/169948 on Oct. 27, 2016 (Inventors—Ahsani et al.; Applicant—Mölnlycke Health Care AB) (8 pages).

(Continued)

*Primary Examiner* — Caitlin A Carreiro

(74) *Attorney, Agent, or Firm* — Ballard Spahr LLP

(57) ABSTRACT

A self-adhesive member for adhering to and covering a portion of a user's skin is disclosed. The self-adhesive member has a backing layer having a self-adhesive coating. The backing layer has a first and a second portion, where the first portion surrounds the second portion, and where the first portion has a first row of slits extending along an outer edge of the backing layer and being distanced a first distance therefrom and the second portion being either void of slits or being provided with fewer slits per area unit than the first portion.

13 Claims, 6 Drawing Sheets

(52) U.S. Cl.
CPC ...... *A61F 13/0226* (2013.01); *A61F 13/0269* (2013.01); *A61F 2013/00119* (2013.01); *A61F 2013/00578* (2013.01); *A61F 2013/00582* (2013.01); *A61F 2013/00859* (2013.01)

(58) Field of Classification Search
CPC ........ A61F 13/0269; A61F 2013/00119; A61F 2013/00578; A61F 2013/00859; A61F 13/00; A61F 13/00008; A61F 13/00021; A61F 13/00089; A61F 13/0266; A61F 13/00085; A61F 13/0246; A61F 13/0253; A61F 13/82; A61F 13/5611; A61F 13/069; A61F 13/512; A61F 2013/00361; A61F 2013/00246; A61F 2013/00251; A61F 2013/00255; A61F 2013/00259; A61F 15/008; A61M 35/00; A61B 46/00; Y10T 428/161; Y10T 428/19; Y10T 428/24298; Y10T 428/24314; B32B 3/266; B32B 3/10; B32B 3/12; B32B 7/06; B42D 1/004; B42D 5/002
USPC ............... 602/47, 57, 58, 59, 54, 41–43, 53; 604/304, 307, 386–387; 128/849, 853, 128/887–894; 428/138, 43, 45, 57, 58, 428/131, 134, 136
See application file for complete search history.

(56) References Cited

U.S. PATENT DOCUMENTS

| | | |
|---|---|---|
| 8,680,360 B2 | 3/2014 | Greener et al. |
| 2005/0147656 A1 | 7/2005 | McCarthy et al. |
| 2014/0094730 A1* | 4/2014 | Greener ............ A61F 13/00038 602/46 |
| 2014/0135721 A1 | 5/2014 | Riesinger |

FOREIGN PATENT DOCUMENTS

| | | | | |
|---|---|---|---|---|
| GB | 821959 A | * | 10/1959 | ......... A61F 13/0203 |
| WO | WO 2006/130594 | | 12/2006 | |
| WO | WO-2006130594 A2 | * | 12/2006 | ............ A61F 13/06 |
| WO | WO-2008/039839 A2 | | 4/2008 | |
| WO | WO-2016/169948 A1 | | 10/2016 | |

OTHER PUBLICATIONS

International Search Report and Written Opinion dated Sep. 21, 2015 by the International Searching Authority for Application No. PCT/EP2015/064544 dated Jun. 26, 2015 and published as WO/2016/030047 on Mar. 3, 2016 (Applicant—Mölnlycke Health Care AB)(10 pages).

* cited by examiner

SELF-ADHESIVE MEMBER

CROSS-REFERENCE TO RELATED APPLICATIONS

The present application is a U.S. National Phase Application of International Application No. PCT/EP2015/064544, filed Jun. 26, 2015, which claims priority to European Application No. 14182641.2, filed Aug. 28, 2014, each of which are hereby incorporated by reference in their entirety.

FIELD OF THE INVENTION

The present invention relates to a self-adhesive member for adhering to and covering a portion of a user's skin, said self-adhesive member comprising a backing layer having a self-adhesive coating.

TECHNICAL BACKGROUND

Self-adhesive wound care products or dressings are frequently used in wound care. Such wound care products typically include a flexible backing layer having an adhesive coating.

For wound care products, stay on ability is an important factor. Adhesive wound care products often have a tendency to start losing the adhesive connection with the user's skin along the edges of the wound care product, due to the friction between the adhesive dressing and materials, such as clothes or bed linen, that the adhesive dressing contact during normal use of it. This is of course undesired, since it may lead to the wound care product being uncomfortable to wear, and to lost function of the product as it may not cover the wound properly.

Hence, there is a need for a self-adhesive wound care product that has an improved stay on ability.

SUMMARY OF THE INVENTION

The object of the present invention is to provide a self-adhesive member that overcomes the above issues.

The general inventive concept is based on the insight that by having a self-adhesive member with at least one row of through openings extending along an outer edge of a backing layer of the self-adhesive member, the self-adhesive member can relax stress imparted by forces subjected to the self-adhesive member from normal wearing such as shear from clothes and/or when a self-adhesive member is being stretched, thereby minimizing the risk of adhesive failure and providing a self-adhesive member having an improved stay-on ability.

A first aspect of the invention relates to a self-adhesive member for adhering to and covering a portion of a user's skin. Said self-adhesive member comprising a backing layer having a self-adhesive coating, said backing layer comprises at least a first and a second portion, wherein said first portion surrounds said second portion, and wherein said first portion comprises at least a first row of slits extending along an outer edge of said backing layer and being distanced a first distance therefrom and said second portion being either void of slits or being provided with fewer slits per area unit than said first portion. By having a first row of slits extending along an outer edge of a backing layer and being distanced a first distance therefrom any stress in the backing layer material as consequence of a force, such as a friction force or stretching, being subjected to the self-adhesive member can be efficiently relaxed such that stretching of the backing layer material, in particular around the outer edge area thereof, is substantially reduced or avoided. That is, the slits of the first row of slits can relax said backing layer when subjected to a force by deforming, e.g. expanding, and thus avoiding and/or minimizing the risk of adhesive failure between the adhesive coating on said backing layer and the skin. As the first row of slits extends along an outer edge of the backing layer, rolling up of edges i.e. adhesive failure between the adhesive coating on the outer edge of the backing layer and the skin can be substantially avoided. For example, if a pair of trousers wear against a standard prior art dressing, the friction between the trouser and such dressing causes a force thereon, which force in case of a standard prior art dressing may result in a stretching of said backing layer and adhesive failure. However, this problem is solved by the self-adhesive member according to the invention, as the slits of the first row of slits can deform or expand when said self-adhesive member is subjected to a force and thus relaxing the stress in the surrounding backing layer material.

That the first portion is provided with slits does not mean that the entire first portion is a large slit. Instead, it means that it is a portion having a multitude of slits, being interrupted by sections of backing layer material. Suitable distributions of slits in the first portion will be further described below in different exemplary embodiments.

Providing a second portion of the backing layer without any slits, or at least with fewer slits than the first portion, and surround said second portion with said first portion has proven to be beneficial. By this, the central portion of the backing layer will be intact, or at least more intact, and thereby provide a sterile barrier close to the wound. Also, dressings most often start detaching at the edges and not centrally. It is therefore not as important to provide for increased relaxation capacity at the central part of the backing layer.

Hence, the through openings of the general inventive concept are according to this first aspect of the present invention slits. A slit is within the context of this application a narrow cut or opening. Preferably, but not necessarily, a slit is provided by cutting the backing layer of the self-adhesive member without removing any material. Hence, a slit is different from e.g. a hole produced by punching or by removing a portion of the material of the backing layer in order to provide e.g. a larger circular or square-shaped opening. The slits extend through said backing layer and its self-adhesive coating. Slits are beneficial from a manufacturing perspective, while they also provide the desired functionality.

According to at least one exemplary embodiment, each of said slits in said first and/or second row of slits is a longitudinally extending slit, wherein a substantially circular through-hole is provided at each end of said slits. Providing the ends of a slit directly adjacent to a respective circular through-hole reduces the risk of tearing of the backing layer at the ends of this slit. Hence, a self-adhesive member being provided with a slit and two circular through-holes according to this embodiment is less susceptible of being ruptured. According to at least one exemplary embodiment, said circular through holes has a respective diameter that is larger than the width of said slit.

According to at least one exemplary embodiment, said slits do not have a straight extension. According to another exemplary embodiment, said slits have a straight extension.

Said first row of slits is a series of slits placed next to each other in a straight or curved line. The shape of the line is dependent on the outer edge of said backing layer of said self-adhesive member since said first row of slits extends along said outer edge.

According to one exemplary embodiment, said second portion is void of slits. It is possible to provide slits in the second portion. However, it is not necessary to provide slits in the second portion in order to fulfil the objectives of the present invention. Therefore, it is conceivable with an exemplary embodiment in which the second portion is void of slits.

According to one exemplary embodiment, said first portion constitutes 10-75 percent of the surface area of said self-adhesive member, more preferably 15-70 percent and most preferably 20-60 percent.

According to one exemplary embodiment, said first portion is smaller than said second portion. As slits in the present invention should be provided along the outer edge of the backing layer of the self-adhesive member, it will in many self-adhesive members be that the first portion is smaller than the second portion.

The percentage rates and proportional relations mentioned above have proven to be beneficial distributions between the first and second portions. The intervals depend, at least partly, on the fact that the relative size of the first portion is larger for a smaller self-adhesive member than for a larger self-adhesive member. This is a consequence of the benefits of providing a sufficiently large area of slits in order to achieve the desired functionality of stress relaxation.

According to one exemplary embodiment, said backing layer of self-adhesive member consists of said first portion and said second portion. Hence, according to this embodiment, the entire area of the backing layer consists of only a first and second portion. It is however conceivable with other layers of the self-adhesive member, and this exemplary embodiment should only be construed to mean that there are no other portions than the first and second portion of the backing layer.

According to at least one exemplary embodiment said slits in said first row of slits are distanced a substantially first uniform distance from said outer edge of said backing layer. It is preferable that approximately all slits in said first row of slits are arranged at a substantially first uniform distance from the outer edge. This way the stress can be relaxed more evenly throughout the extension of said first row of slits.

According to at least one exemplary embodiment each slit in said first row of slits are distanced a substantially first uniform distance from said outer edge of said backing member.

According to at least one exemplary embodiment said uniform distance between each slit in said first row of slits and said outer edge is between an edge or an edge point of said slit, which is closest to said outer edge, and said outer edge. This ensures that said slits are not open at said outer edge of the backing layer. In other words said slits are surrounded by said backing layer. An edge point is a point or several points of said slit's edge which is arranged closest to said outer edge in a direction perpendicular to said outer edge.

According to at least one exemplary embodiment said substantially first uniform distance between each slit in said first row of slits and said outer edge is between 2 and 10 mm, preferably between 2.5 and 8 mm, and more preferably 3-7 mm.

According to at least one exemplary embodiment said first portion of said backing layer further comprises a second row of slits extending in a direction along said first row of slits and distanced from said outer edge of said backing layer with a second distance, which second distance is greater than said first distance between said first row of slits and said outer edge. By having a second row of slits at a second distance from said outer edge, which second distance is greater than said first distance, two distinct rows of slits may be created. Said second row of slits is, hence, arranged at a position further away from said outer edge. As for the first row of slits, the second row of slits assists in relaxing any stress in the backing layer material. That is, the slits of the second row of slits can relax the backing layer when subjected to a force by deforming, e.g. expanding, and thus avoiding and/or minimizing the risk of adhesive failure between the adhesive coating on the backing layer and the skin. By providing two rows of slits, stretching of the backing layer material, in particular around the outer edge area thereof, is even further reduced or avoided. The definition of said second row of slits and its slits is the same as for said first row of slits.

According to at least one exemplary embodiment said slits in said second row of slits are distanced a substantially uniform second distance from said outer edge of said backing layer. It is preferable that approximately all slits in said second row of slits are arranged at a substantially second uniform distance from said outer edge. This way the stress may be relaxed more evenly throughout the extension of said second row of slits.

According to at least one exemplary embodiment said substantially uniform second distance between each slit in said second row of slits and said outer edge of said backing layer is between 4-20 mm, preferably between 5-16 mm, and more preferably 6-14 mm. Said second distance has to be chosen dependent on the shape of said slits so that said slits of said second row of slits does not overlap with said slits in said first row of slits and hence together form only one slit. In other words said slits in said second row of slits are also surrounded by said backing layer and there is a distance between the holes in said first row of slits and the holes in said second row of slits.

According to at least one exemplary embodiment said first portion of said backing layer further comprises a second row of slits extending in a direction along said first row of slits and said slits in said second row of slits are distanced a uniformly spaced third distance to each proximal slit in said first row of slits.

According to at least one exemplary embodiment said uniformly spaced third distance is between 2-10 mm, preferably between 2.5-8 mm, and more preferably 3-7 mm. Said uniformly spaced third distance is to be measured between one slit in said second row of slits and a proximal slit in said first row of slits in a direction which is perpendicular to said outer edge.

According to at least one exemplary embodiment said uniformly spaced third distance between each slit in said second row of slits and each proximal slit in said first row of slits is between an edge or an edge point of each slit in said second row of slits and an edge or an edge point of each proximal slit in said first row of slits facing each other. This ensures that the two rows of slits are separated from each other. An edge point is a point or several points of said slit edge which is arranged closest to said outer edge or to another slit in another row.

According to at least one exemplary embodiment said backing layer further comprises a second row of slits extending in a direction along said first row of slits and said slits in said second row of slits are arranged at an overlapping uniformly spaced fourth distance to each proximal slit in said first row of slits. This means that said slits in said second row of slits overlaps two proximal slits with said fourth distance in a perpendicular direction to said outer edge. If said outer edge is rounded said distance is to be measured perpendicular to a line tangent to said outer edge such that said distance is as small as possible.

According to at least one exemplary embodiment each slit of said second row of slits and said first row of slits is arranged offset relative to one another. This means that a slit in said second row of slits is staggered relative a proximate slit in said first row of slits. In other words, they are not arranged next to each other. Together the slits in said first and said second row of slits may be arranged in a zig-zag line.

According to at least one exemplary embodiment each slit of said second row of slits and said first row of slits is arranged offset relative to one another such that the centre of substantially all slits of said second row of slits are arranged intermediate of two proximal slits of said first row of slits. This enables that said slits in said first and said second rows of slits may be evenly arranged relative each other and the stress can be relaxed evenly along said rows of slits.

According to at least one exemplary embodiment said slits in said second row of slits, which have their respective centres arranged intermediate of two proximal slits of said first row of slits, each has a longitudinal extension which is at least as long as the distance between said two proximal slits of said first row of slits. This enables that each slit in said second row of slits is large enough to cover, i.e. has an extension which covers, the portions between said slits in said first row of slits. This ensures that the extension of said outer edge where said first and said second row of slits are arranged does not have a portion where no slits are present. By this, the relaxation of stresses in said self-adhesive member may be even further improved.

According to at least one exemplary embodiment, said slits in said second row of slits, which have their respective centres arranged intermediate of two proximal slits of said first row of slits, each has a longitudinal extension which is at least 20 percent, more preferably at least 30 percent and most preferably at least 40 percent longer than the distance between said two proximal slits of said first row of slits.

According to at least one exemplary embodiment said slits in said first and/or second row of slits have uniform shapes. The advantages of having the same uniform shape of all the slits in one row of slits are mainly from a manufacturing perspective as it is more efficient to make only one sort of slits.

According to at least one exemplary embodiment each of said slits in said first and/or second row of slits has a length which is between 2 and 10 mm, preferably between 3 and 8 mm, and more preferably 4-6 mm. The longer said slits are the more flexible said backing layer gets, but at the same time the risk of tearing said backing layer apart increases. The ranges above have proven to be beneficial both in terms of flexibility, stress relaxation and robustness.

It is conceivable with embodiments in which said length of said slits within said first row of slits may differ from each other. It is also conceivable with embodiments in which said length of said slits within said second row of slits may differ from each other. Alternatively, the length of said slits in said first row of slits may differ from the length of said slits in said second row of slits. Advantages of the different embodiments mentioned are that it is possible to better control the relaxation of stress within the self-adhesive member. Some self-adhesive members are configured to be positioned in a certain orientation on a user's skin, and the forces acting upon such self-adhesive members may vary between different areas of the self-adhesive member. It may therefore be advantageous to control the stress relaxation so that it is higher in the areas where a larger amount of stress is present.

According to at least one exemplary embodiment said slits within said first row of slits and/or said slits within said second row of slits are arranged at a distance from each other which is between 2 and 10 mm, preferably between 3 and 8 mm, and more preferably 4-6 mm.

According to at least one exemplary embodiment said self-adhesive member has a square shape and said first row of slits and/or said second row of slits is/are arranged on at least two opposite sides of said self-adhesive member. By arranging said first and/or the second row of slits on two opposite sides of a square-shaped self-adhesive member the rows of slits when arranged on a body may be arranged in the direction where the skin will stretch. As a consequence, when a user for example bend his/her knee the material, i.e. said backing layer, between said slits will stretch together with the skin it is attached to and said slits will deform and thereby relax the stress that is induced to the self-adhesive member.

According to at least one exemplary embodiment said first row of slits and/or said second row of slits is/are arranged around a periphery of said self-adhesive member. By arranging said rows of slits around the whole periphery, said self-adhesive member can be arranged on the wound site in any direction and some of said slits in said row of slits will be arranged in a correct direction in order to relax the stresses. That is, when applying said self-adhesive member to a user, no care has to be taken in order to arrange it correctly.

According to at least one exemplary embodiment, the slits of the first and second row of slits are provided such that it is not possible to draw an imaginary line in the plane of the self-adhesive member, extending from an outer edge of the self-adhesive member to another outer edge of the self-adhesive member, which line is perpendicular to the outer edge of said self-adhesive member, without intersecting at least one slit. Hence, a force acting on the self-adhesive member in the plane of the self-adhesive member and perpendicular to the direction of the outer edge of the self-adhesive member will not be able to pass said self-adhesive member without passing at least one of said slits, and thereby become at least partly relaxed.

According to at least one exemplary embodiment said slits in said first and/or second row of slits have an elongated shape, and wherein at least 80 percent, preferably at least 90 percent, more preferably at least 95 percent, and most preferably all of the slits has their major longitudinal extension in the same direction as the extension of the outer edge of the self-adhesive member that each slit is closest to. This way less slits are necessary throughout the extension of the outer edge. Further, the slits, depending on where they are arranged on said self-adhesive member and how it is attached to the body, may be arranged in the direction where the stretching of the skin will take part or where the friction between said self-adhesive member and the materials, such as clothes or bed linen, is applied or is the largest. Said slits will deform by being stretched during use.

According to at least one exemplary embodiment said self-adhesive member further comprises a central area and an edge area comprising said outer edge. In said central area a wound pad can be arranged and said rows of slits are arranged on said edge area. Preferably said rows of slits are arranged closer to said outer edge than an outer edge of said central area.

According to at least one exemplary embodiment, said central area coincides with said second portion and said edge area coincides with said first portion.

According to at least one exemplary embodiment said self-adhesive member further comprises a wound pad attached to said backing layer distanced from said outer edge of said backing layer; and said substantially uniform first distance between said slits in said first row of slits and said outer edge of said backing layer is shorter than a fifth distance between said slits in said first row of slits and an outer edge of said wound pad.

According to at least one exemplary embodiment said substantially uniform second distance between said slits in said second row of slits and said outer edge of said backing layer is shorter than a sixth distance between said slits in said second row of slits and said outer edge of said wound pad. It is advantageous that said slits in said first and/or said second row of slits are arranged closer to said outer edge than to an outer edge of said wound pad. This to ensure that said self-adhesive member is properly attached to the body so that it does not start detaching from the user's skin along its outer edge and that said backing layer seals properly around said wound pad when it is attached to the wound site so that no leakage occurs through said slits. It is however also important that said slits are not too close to said outer edge as that may increase the risk of rupture of said backing layer.

According to another exemplary embodiment, said self-adhesive member is not limited to have only one or two rows of slits. Three or four rows of slits or even more is also possible.

According to one exemplary embodiment, all of said rows of slits are provided in the first portion of said backing layer.

According to one exemplary embodiment, said backing layer is made of a material, or a combination of materials, such as a laminate, chosen from a group of polyester, polyurethane, ethylene vinyl acetate, thermoplastic elastomer, silicone film and elastic non-woven materials.

According to one exemplary embodiment, the backing layer has a thickness of 10-100 microns, more preferably 10-50 microns and most preferably 15-30 microns.

According to one exemplary embodiment, said self-adhesive member has a backing layer of polyurethane film, a thickness of 15-30 microns, and is provided with two rows of slits, wherein the slits have a length of 5 mm and are provided 3 mm from an adjacent slit in the same row of slits. Furthermore, the distance between the two rows of slits is 5 mm.

According to a second aspect of the present invention, a self-adhesive member for adhering to and covering a portion of a user's skin is provided. Said self-adhesive member comprising a backing layer having a self-adhesive coating, wherein said backing layer comprises at least a first row of through openings extending along an outer edge of said backing layer and being distanced a first distance therefrom.

Hence, according to the second aspect of the present invention, the through openings are provided along an outer edge of said backing layer. Said through holes are openings in the backing layer which extends through said backing layer and its self-adhesive coating. The through openings may be either slits or through holes. A slit is within the context of this application a narrow cut or opening. Preferably, but not necessarily, a slit is provided by cutting the backing layer of the self-adhesive member without removing any material. A through hole, on the other hand, may have any shape and includes also through openings in which material has been removed, for example by punching or cutting.

By having a first row of through openings extending along an outer edge of a backing layer and being distanced a first distance therefrom any stress in the backing layer material as consequence of a force, such as a friction force or stretching, being subjected to the self-adhesive member can be efficiently relaxed such that stretching of the backing layer material, in particular around the outer edge area thereof, is substantially reduced or avoided. That is, the through openings of the first row of through openings can relax said backing layer when subjected to a force by deforming, e.g. expanding, and thus avoiding and/or minimizing the risk of adhesive failure between the adhesive coating on said backing layer and the skin. As the first row of through openings extends along an outer edge of the backing layer, rolling up of edges i.e. adhesive failure between the adhesive coating on the outer edge of the backing layer and the skin can be substantially avoided. For example, if a pair of trousers wear against a standard prior art dressing, the friction between the trouser and such dressing causes a force thereon, which force in case of a standard prior art dressing may result in a stretching of said backing layer and adhesive failure. However, this problem is solved by the self-adhesive member according to the invention, as the through openings of the first row of slits can deform or expand when said self-adhesive member is subjected to a force and thus relax the stress in the surrounding backing layer material.

According to at least one exemplary embodiment each of said through openings in said first and/or second row of through openings is a through hole, having a cross-section, which is oval or square-shaped. Oval or square-shaped through holes have the benefit of reducing the risk of tear of the backing layer. The through holes having an oval or square-shaped cross-section preferably have a width which is between 2 and 10 mm, preferably between 3 and 8 mm, and more preferably 4-6 mm.

According to one exemplary embodiment, said backing layer comprises at least a first and a second portion, wherein said first portion surrounds said second portion, and wherein said first portion comprises at least said first row of through openings, and said second portion being either void of through openings or being provided with fewer through openings per area unit than said first portion.

The second aspect of the present invention may also be freely combined with the different exemplary embodiments mentioned above in relation to the first aspect of the present invention. Hence, the through holes of the second aspect of the present invention may e.g. be slits in accordance with the different exemplary embodiments mentioned above. Furthermore, the through openings according to this second aspect of the present invention may but need not be slits and may have the other characteristics and/or be provided similar to the exemplary embodiments mentioned above for the first aspect of the present invention in which the through openings are slits. For example, but not limited to, the positions of the through openings, both relative each other and also relative the backing layer, the number of rows of through openings and their relative positions, and the sizes of the through openings may be the same. Furthermore, the self-adhesive member of the second aspect of the present invention may have the same characteristics as mentioned above in different exemplary embodiments of the self-adhesive member of the first aspect of the present invention. For example, but not limited to, the shape and design of the self-adhesive member and the relative sizes of the first and second portions may be the same.

Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of said element, device, component, means, step, etc., unless explicitly stated otherwise.

Other objectives, features and advantages of the present invention will appear from the following detailed disclosure, as well as from the drawings.

BRIEF DESCRIPTION OF THE DRAWINGS

The above, as well as additional objects, features and advantages of the present invention, will be better understood through the following illustrative and non-limiting detailed description of exemplary embodiments of the present invention, with reference to the appended drawings, where the same reference numerals will be used for similar elements, wherein:

FIG. 1b shows cross-section A-A of the self-adhesive member in FIG. 1a.

FIG. 2a shows an enlarged partial top view from the cut out B in FIG. 1a.

FIGS. 2b-2i show different embodiments of the first and second rows of through openings on the self-adhesive member shown in FIG. 2a.

All the figures are highly schematic, not necessarily to scale, and they show only parts which are necessary in order to elucidate the invention, other parts being omitted or merely suggested.

DETAILED DESCRIPTION OF EXEMPLARY EMBODIMENTS

Embodiments of the invention will be described in more detail in the following with reference to the accompanying drawings.

Figure 1A:
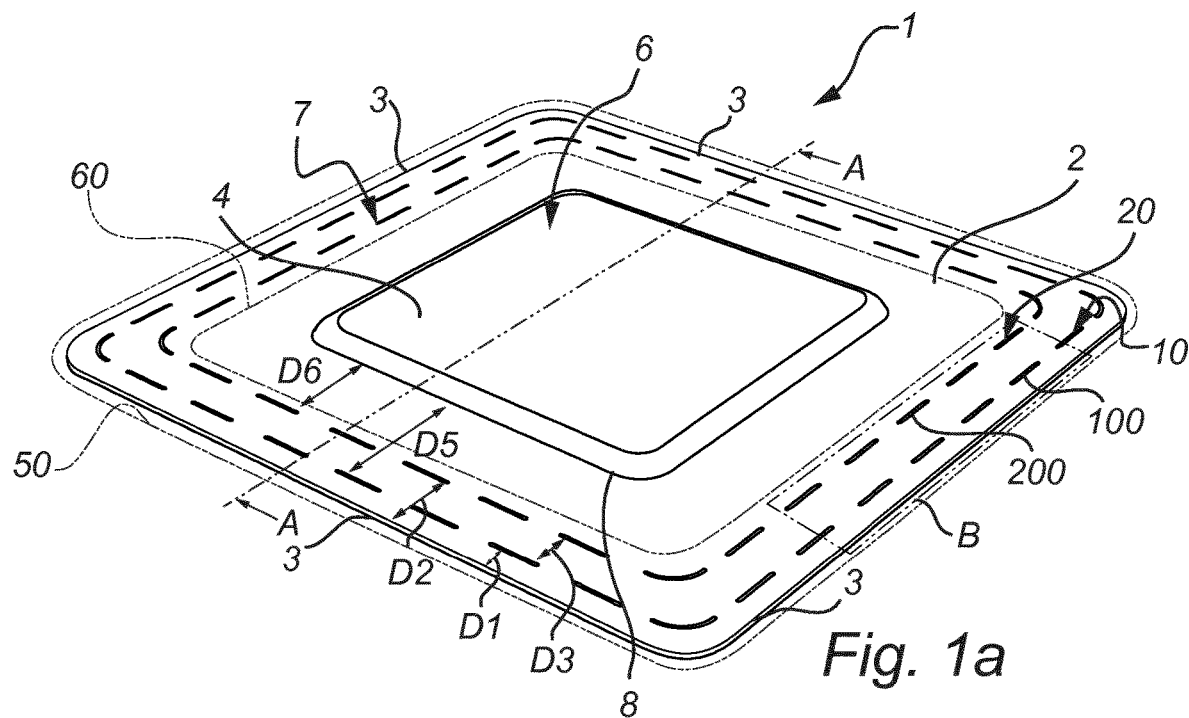
FIG. 1a shows a self-adhesive member according to an embodiment of the invention in perspective.
Figure 1B:
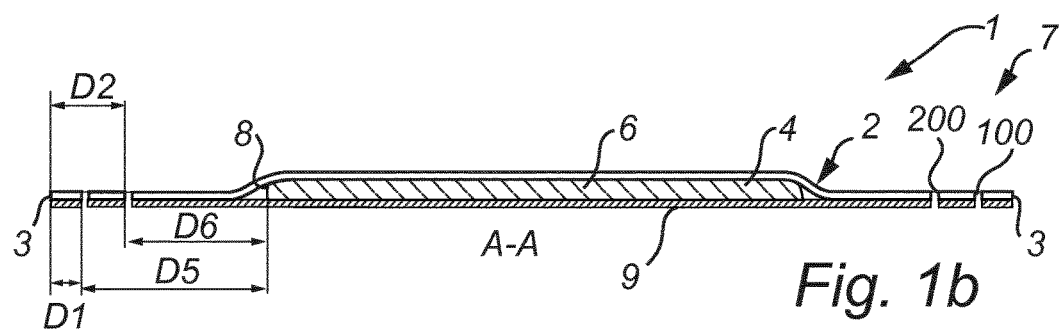

FIG. 1a shows a square-shaped self-adhesive member 1 for adhering to and covering a portion of a user's skin, such as a self-adhesive wound care product. FIG. 1b shows the cross-section A-A in FIG. 1a and hence, they will be described together. Line A-A also represents an imaginary line extending from an outer edge of the self-adhesive member to another outer edge of the self-adhesive member. The self-adhesive member 1 is not limited to have a square shape, it may have any other suitable shape, such as round, oval etc.

The self-adhesive member 1 comprises a backing layer 2 having a self-adhesive coating 9, preferably a silicone-gel adhesive coating although other adhesive coatings are conceivable such as polyurethanes acrylic adhesives or rubber based or acrylic based soft hotmelt coating.

The backing layer 2 is a flexible layer, which can readily be applied to any part of the wearer's body. The backing layer is suitably a polymer film, preferably a polyurethane film, as such films are suitable for this purpose. The plastic film, in particular the polyurethane film, may have a thickness of less than 100 μm, preferably 10-50 μm, in order to allow the wound care product to adapt closely to the shape of the wearer's body. The backing layer 2 may alternatively be a laminate, which could suitably include an elastic film made of for example polyurethane (PU), ethylene vinyl acetate (EVA) or thermoplastic elastomer (TPE). The laminate could also include a layer of nonwoven or textile material. The layers of the laminate may be laminated by adhesive lamination, using for example hotmelt or acrylic glue, heat lamination or flame lamination.

A carrier layer (not shown) may also be provided on the backing layer, in order to facilitate handling of the wound care product. The function of the carrier layer is to support the plastic film and to provide steadiness, while applying the wound care product to the wearer's skin, whereupon the carrier layer is removed. Such carrier layer may be a plastic film of somewhat higher stiffness than the material used for the backing layer, or nonwoven material, flexible foam material, or paper, which advantageously is polyethylene-coated, or the like.

The solution provided by this invention is particularly suitable when the wound care product is a ready-to-use product, such as pre-cut products which come in ready-to-use sizes, adhesive wound care tapes, film dressings and other ready for use dressings, and ostomy products, such as base plates.

The backing layer 2 has an outer edge 3 which extends all around the self-adhesive member 1. A wound pad 4 is arranged at a central area 6 of said self-adhesive member 1, and it will be in contact with the wound during use. An edge area 7 comprising the outer edge 3 surrounds the central area 6. The self-adhesive member 1 is not limited to have a wound pad, instead the self-adhesive member 1 can be connected to a bag at the central area to receive waste, for example, as part of an ostomy appliance (not shown). It can also be used in e.g. film dressings for negative pressure wound therapy, electrodes for electrostimulation of wounds, skin prevention dressings, dressings for prevention of pressure ulcers and/or dressings containing anti-microbial substances.

The backing layer 2 comprises a first portion 50 and a second portion 60. The first portion 50 comprises a first row of through openings 10, which extends along said outer edge 3 of said backing layer 2 around the whole self-adhesive member 1 and it is arranged at a first distance D1 from said outer edge 3 (see also FIG. 2a). The first distance D1 is between 2-10 mm, preferably between 2.5-8 mm, and more preferably 3-7 mm. In other words the first portion 50, and thereby the first row of through openings 10 is arranged on the edge area 7. The second portion 60 is void of any through openings.

Figure 1C:
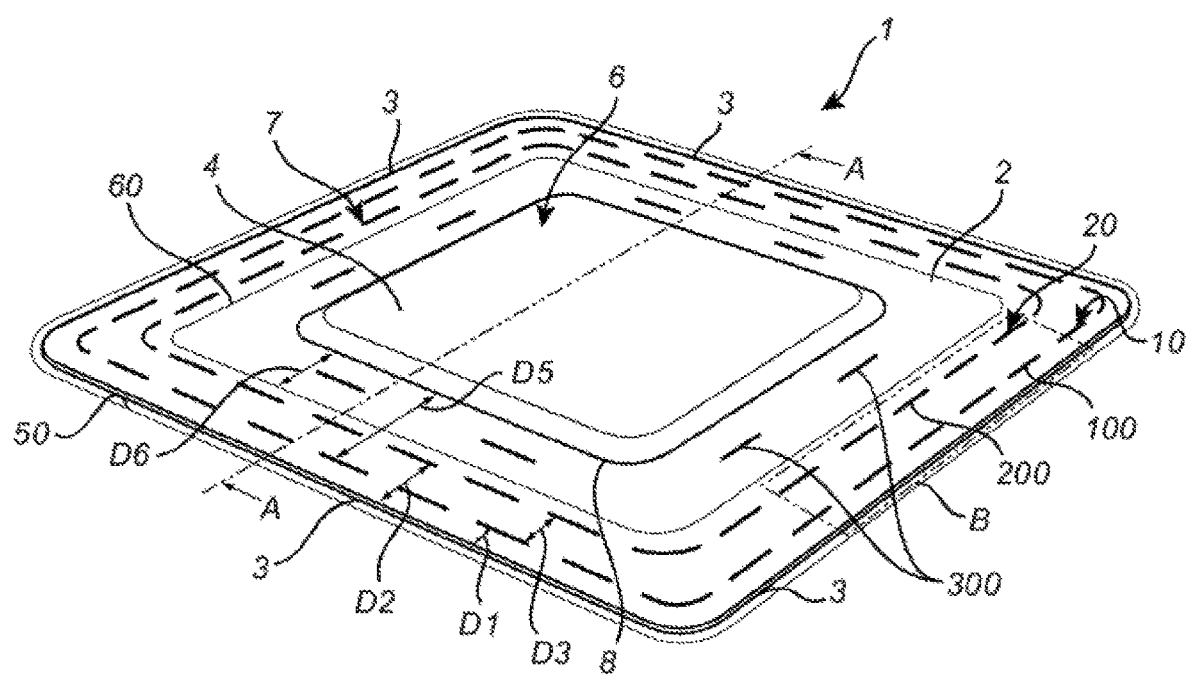
FIG. 1c shows a self-adhesive member according to an embodiment of the invention in perspective.

FIG. 1c is identical to FIG. 1A except that second portion 60 is shown as being provided with fewer slits 300 per area unit than said first portion 50. In FIG. 1a the second portion 60 is shown as being void of slits.

The through openings 100 of said first row of through openings 10 have a uniform shape and size and they are arranged equally spaced around the self-adhesive member 1.

The backing layer 2 also comprises a second row of through openings 20, which are also provided in said first portion 50 and extending along said outer edge 3 of said backing layer 2 and it is arranged at a second distance D2 from said outer edge 3. The second distance D2 between the second row of through openings 20 is greater than said first distance D1 between said first row of through openings 10 and said outer edge 3.

The through openings 200 of said second row of through openings 20 are also uniform in size and shape and they are arranged equally spaced around the self-adhesive member 1. They are in this embodiment also uniform to the openings 100 of the first row of through openings 10.

The second distance D2 is between 4-20 mm, preferably between 5-16 mm, and more preferably 6-14 mm. In other words the second row of through openings 20 is also arranged on the edge area 7. The first distance D1 between said through openings 100 in said first row of through openings 10 and said outer edge 3 of said backing layer is shorter than a fifth distance D5 between said through openings 10 in said first row of through openings 100, measured from said through opening edge closest to said outer edge 3 of said self-adhesive member 1, and an outer edge 8 of said wound pad 4. The second distance D2 between the through openings 200 in said second row of through openings 20 and said outer edge 3 of said backing layer 2 is shorter than a sixth distance D6 between the through openings 200 in said second row of through openings 20, measured from said through opening's edge closest to said outer edge 3 of said self-adhesive member 1, and said outer edge 8 of said wound pad 4.

Figure 2A:
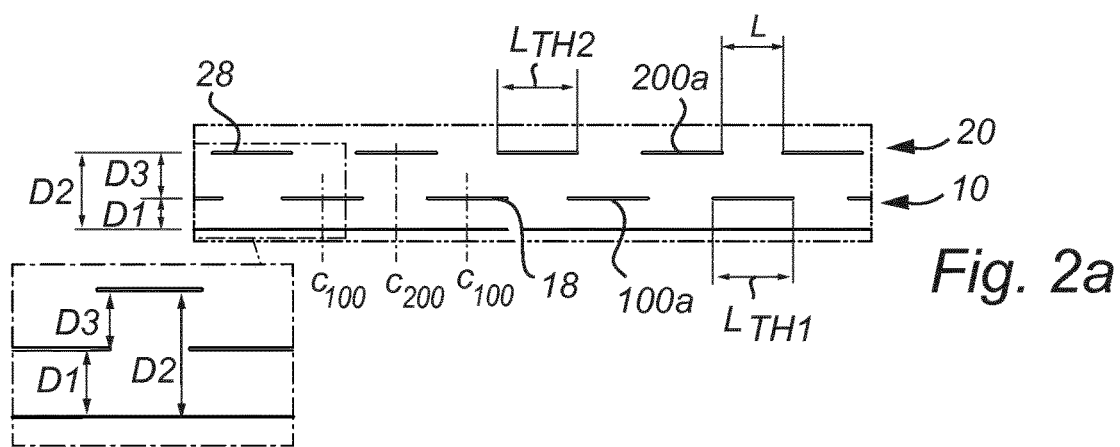

FIG. 2*a* shows an enlarged view of a first embodiment of the first row of through openings 10 and the second row of through openings 20 at the area B in FIG. 1*a*, i.e. a part of the first portion 50 is illustrated. The through openings in this embodiment are uniform straight slits 100*a*. If the self-adhesive member is rounded or has rounded parts, the slits may have the same roundness such that they, at least along the major portion of their extension, follow the edge of the backing layer. The slits 100*a* are extending in the longitudinal direction of the outer edge 3. Each slit 100*a*, 200*a* is essentially parallel with the outer edge 3, which is essentially a straight edge. At the corners (see FIG. 1), the slits 100*a* in this embodiment follow the contour of outer edge. Alternatively, the slits in the corners may be omitted.

The first distance D1 between each slit 100*a* in said first row of through openings 10 and said outer edge 3 is to be measured between an edge 18 of the slit 100*a*, closest to the outer edge 3 of the backing layer 2.

The second distance D2 between each slit 200*a* in said second row of through openings 2 and said outer edge 3 is to be measured between an edge 28 of the slit 200*a* closest to the outer edge 3 of the backing layer 3.

Alternatively, said slits 200*a* in said second row of through openings 20 are distanced a uniformly third spaced distance D3 to each proximal slit 100*a* in said first row of through openings 10. Said uniformly third spaced distance D3 between each slit 200*a* in said second row of through openings 20 and each proximal slit 100*a* in said first row of through openings 10 is between 2-10 mm, preferably between 2.5-8 mm, and more preferably 3-7 mm. The distance D3 is to be measured in the perpendicular direction to the outer edge.

Each slit 200*a*, 100*a* of said second row of through openings 20 and said first row of through openings 10 is arranged offset relative to one another.

It is exemplified that each slit 200*a*, 100*a* of said second row of through openings 20 and said first row of through openings 10 is arranged offset relative to one another such that the centre C$_{200}$ of substantially all slits 200*a* of said second row of through openings 20 are arranged intermediate of two proximal slits 100*a* of said first row of through openings, i.e. the centre C$_{200}$ of one slit 200*a* in said second row of through openings 20 is arranged in the middle i.e. at half the distance, between the centres C$_{100}$ of two proximal arranged slits 100*a* in said first row of through openings 10. Each slit 200*a* of the second row of through openings 20 has an longitudinal extension, i.e. a length L$_{TH2}$, which is at least so long as the distance L between said two proximal slits 100*a* of said first row of through openings 10. Each slit 100*a* of the first row of through openings 10 has an longitudinal extension L$_{TH1}$ which is at least so long as the distance L between said two proximal slits 200*a* of said second row of through openings 20. Preferably, they are longer so the slits 100*a*, 200*a* overlap each other.

Each of said slits 100*a*, 200*a*, in said first and/or second row of through openings 10, 20 has a length L$_{TH1}$, L$_{TH2}$ which is between 2-10 mm, preferably between 3-8 mm, and more preferably 4-6 mm, which is to be measured in the longitudinal direction of the outer edge.

Figure 2B:
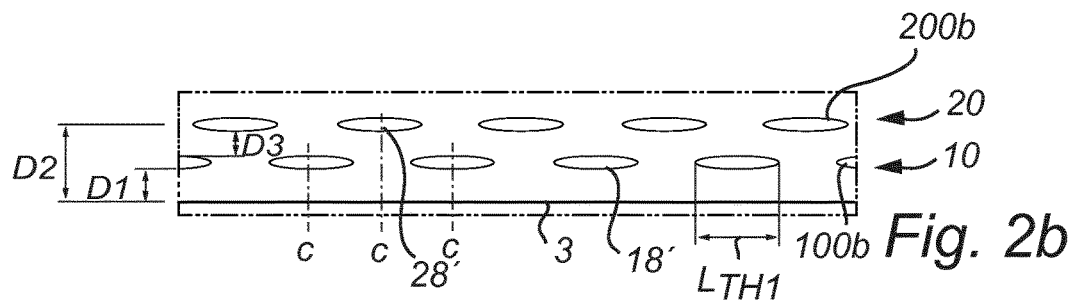

FIG. 2*b* shows a part of the first portion 50 with the through openings of the first row of through openings 10 and the second row of through openings 20 as uniform oval through holes 100*b*, 200*b*. However, the positions and the distances relative the through holes 100*b*, 200*b* in the first row of through openings 10 and the second row of through openings 20 are the same as described for the slits in FIG. 2*a*. However, the first distance D1 between each through hole 100*b* in said first row of through openings 10 and said outer edge 3 is to be measured between an point, i.e. edge point 18' of the through hole closest to the outer edge 3 of the backing layer 2 in a direction perpendicular to said outer edge 3.

The second distance D2 between each through hole 200*b* in said second row of through openings 20 and said outer edge 3 is to be measured between a point, i.e. an edge point 28' of the through hole 200*b* closest to the outer edge 3 of the backing layer 2 in a direction perpendicular to said outer edge 3.

Figure 2C:
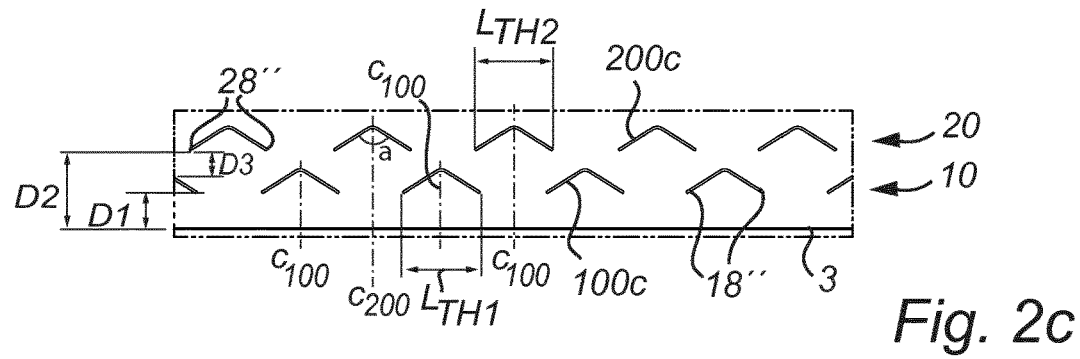

FIG. 2*c* shows a part of the first portion 50 with the through openings of the first row of through openings 10 and the second row of through openings 20 as uniform V-shaped slits 100*c*, 200*c* where the tip of the V is in the centre C$_{100}$, C$_{200}$ and pointing in the opposite direction to the outer edge 3, i.e. it is pointing towards the central area of the self-adhesive member 1. The positions and the distances relative the slit 100*c*, 200*c* in the first row of through openings 10 and the second row of through openings 20 are the same as described for FIG. 2*a*. However, the first distance D1 between each slit 100*c* in said first row of through openings 10 and said outer edge 3 is to be measured between an edge point 18" of the slit 100*c* closest to the outer edge 3 of the backing layer 2. In this case there are two edge points 18" and each edge point 18" is arranged at a distance D1 from said outer edge 3.

The second distance D2 between each slit 200*c* in said second row of through openings 20 and said outer edge 3 is to be measured between an edge point 28" of the slit 200 closest to the outer edge 3 of the backing layer 2. In this case there are two points, edge points 28" and each edge point 28" are arranged at distance D2 from said outer edge 3. The length L$_{TH1}$, L$_{TH2}$ of the slits 100*c*, 200*c* are to be measured between the opening of the V, i.e. the distance between the two edge points, 18" of the slits 100*c* in the first row of through openings 10, and between the two edge points, 28" of the slits 200*c* in the second row of through openings 20. The angle α between the legs of the V-shaped slit is between 45°-175°, preferably between 60°-140°, more preferably 70°-120° and even more preferably between 85°-105°.

Figure 2D:
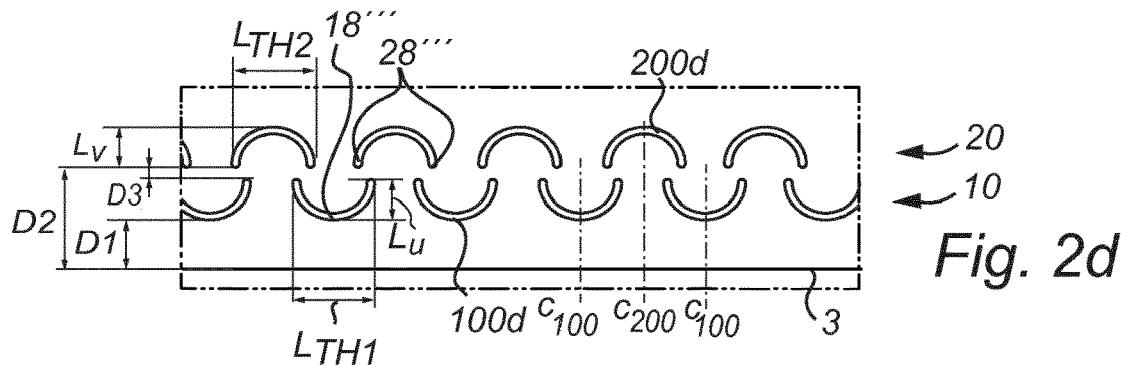

FIG. 2*d* shows a part of the first portion 50 with the through openings of the first row of through openings 10 and the second row of through openings 20 as uniform U-shaped slits 100*d*, 200*d*, where the openings of the U's of the first row of through openings 10 are facing the openings of the U's of the second row of through openings 20. The bottom of the U's are centres $C_{100}$, $C_{200}$ and the bottoms of the U's of the first row of slits 100*d* are pointing towards the outer edge 3, while the bottoms of the U's of the second row of through openings 20 are pointing in the opposite direction. The positions and the distances relative the slits 100*d*, 200*d* in the first row of through openings 10 and the second row of through openings 20 are the same as described for FIG. 2*a*. However, the first distance D1 between each slit 100*d* in said first row of through openings 10 and said outer edge 3 is to be measured between an edge point 18''' of the slit 100*d* closest to the outer edge 3 of the backing layer 2, i.e. the bottom point 18''' of the U. The second distance D2 between each slit 200*d* in said second row of through openings 20 and said outer edge 3 is to be measured between an edge point 28''' of the slit 200 closest to the outer edge 3 of the backing layer 2. In this case there are two edge points 28''' and each edge point 28''' is arranged at said second distance D2 from said outer edge 3. The length $L_{TH1}$, $L_{TH2}$ of the slits 100*d*, 200*d* are to be measured between the opening of the U. The depth $L_U$ of the U-shaped slits 100*d*, 200*d* is to be measured between the bottom of the U and the opening of the U shaped slit in the direction perpendicular to the outer edge. If the outer edge is rounded it will be in a direction perpendicular to a line which is tangential to the outer edge.

Figure 2E:
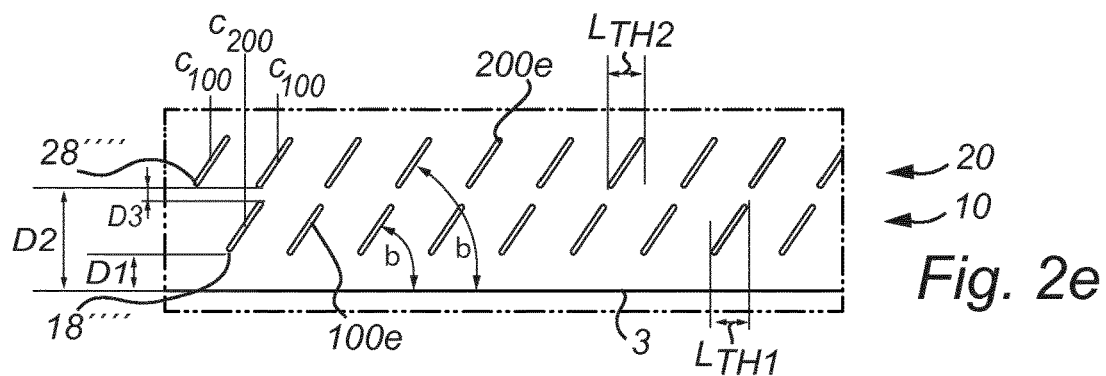

FIG. 2*e* shows a part of the first portion 50 with the through openings of the first row of through openings 10 and the second row of through openings 20 as uniform slits 100*e*, 200*e*. Each slit is arranged in an angle to the outer edge 3. The angle β is between 5°-70°, preferably between 10°-60°, and more preferably 20°-50°. The centres $C_{100}$, $C_{200}$ of each slit 100*e*, 200*e* is at half the length of the slits 100*e*, 200*e* in the longitudinal direction of the outer edge. The positions and the distances relative the slits 100*e*, 200*e* in the first row of through openings 10 and the second row of through openings 20 are the same as described for FIG. 2*a*. However, the first distance D1 between each slit 100*e* in said first row of through openings 10 and said outer edge 3 is to be measured between an edge point, i.e. edge point 18'''' of the slit closest to the outer edge 3 of the backing layer 2.

The second distance D2 between each slit 200*e* in said second row of through openings 20 and said outer edge 3 is to be measured between a point, i.e. an edge point 28'''' of the slit 200*e* closest to the outer edge 3 of the backing layer 2. The length $L_{TH1}$ of the slits 100*e* in said first row of through openings 10 is to be measured in the longitudinal direction of the outer edge 3 between the edge point 18'''' and the edge point which is positioned furthest away from the outer edge 3. The length $L_{TH2}$ of the slits 200*e* in said second row of through openings 20 is to be measured in the longitudinal direction of the outer edge 3 between the edge point 28'''' and an edge point which is positioned furthest away from the outer edge 3.

Figure 2F:
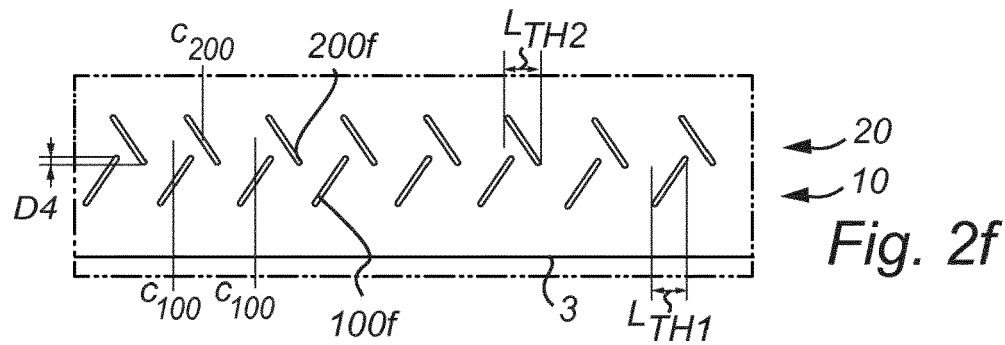

FIG. 2*f* shows a part of the first portion 50 with similar uniform angled slits as the through openings of the first row of through openings 10 and the second row of through openings 20 in FIG. 2*e* except that the slits 200*f* in the second row of through openings 20 are angled in the opposite direction to the slits 100*f* in the first row of through openings 10. Further, the slits 200*f* of the second row of through openings are not distanced a uniformly third spaced distance to each proximal slit in said first row of through openings. In this exemplary embodiment the slits 100*f*, 200*f* of the first and the second row of through openings are overlapping each other in the perpendicular direction to the outer edge. They overlap each other with a fourth distance D4 which is 1-10 mm, preferably 2-8 mm and more preferably 3-7 mm.

Figure 2G:
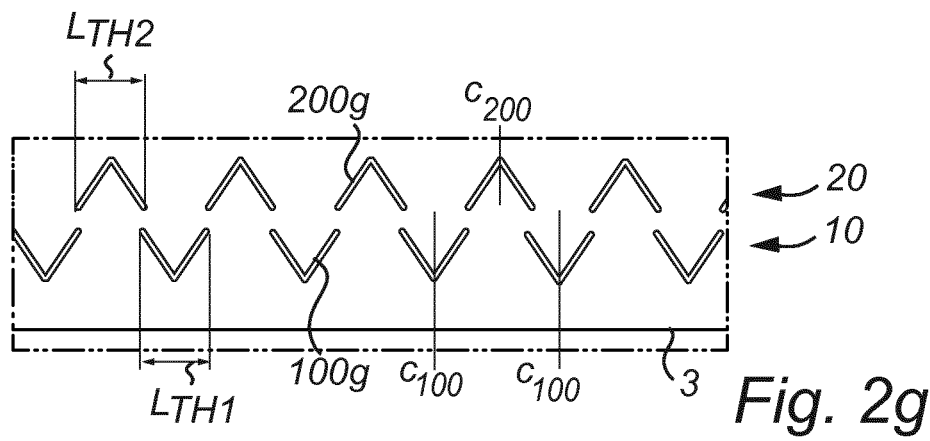

FIG. 2*g* shows a part of the first portion 50 with similar uniform V-shaped slits 100*g*, 200*g* as the through openings of the first row of through openings 10 and the second row of through openings 20 in FIG. 2*c* except that the tip of the slits 100*g* in the first row of through openings 10 are pointing in the direction toward the outer edge 3. That is the openings of the V's are pointing toward each other.

Figure 2H:
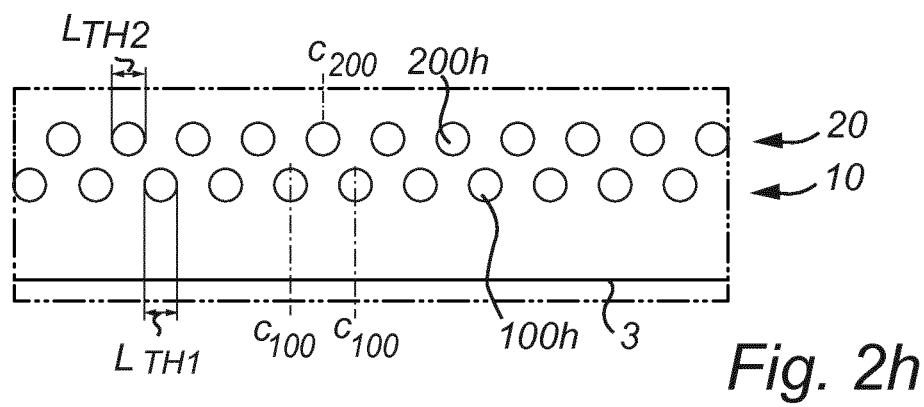

FIG. 2*h* shows a part of the first portion 50 with similar through openings of the first row of through openings 10 and the second row of through openings 20 as in FIG. 2*b*, except that the through holes 100*h*, 200*h* are round. The diameter of the round through holes 100*h*, 200*h* is the same as the length $L_{TH1}$ of the through holes measured in the longitudinal direction of the outer edge 3.

Figure 2I:
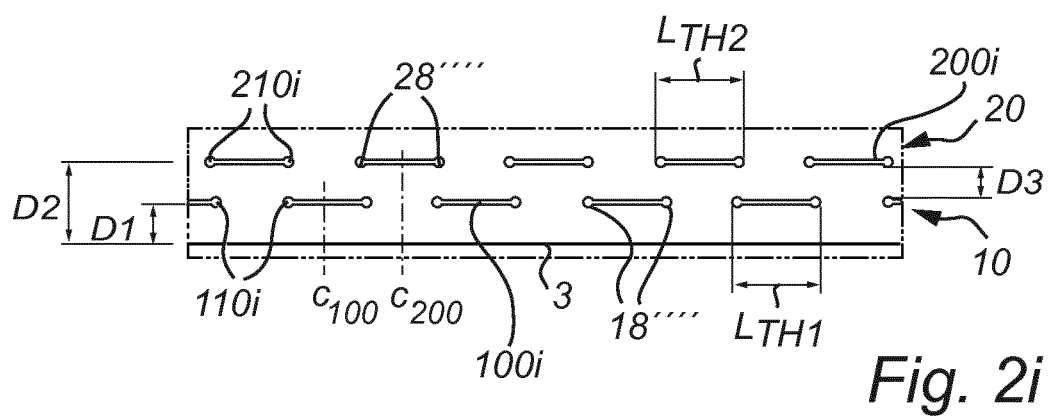

FIG. 2*i* shows a part of the first portion 50 with the through openings of the first row of through openings 10 and the second row of through openings 20 as slits 100*i*, 200*i* being provided adjacent a circular through-hole 110*i*, 210*i* at each end. Hence, the resulting shape of the through openings is uniform dog bone shaped through openings. The diameters of the circular through holes 110*i*, 210*i*, are somewhat larger than the width of the longitudinally extending slits 100*i*, 200*i*. The positions and the distances relative the through openings in the first row of through openings 10 and the second row of through openings 20 are the same as described for FIG. 2*a*. However, the first distance D1 between each through opening 100*i*, 110*i* in said first row of through openings 10 and said outer edge 3 is to be measured between an edge point 18'''' of the through opening 100*i*, 110*i* closest to the outer edge 3 of the backing layer 2. In this case there are two edge points 18'''' and each edge point 18'''' is provided at a circular through hole 110*i* and is arranged at a distance D1 from said outer edge 3.

The second distance D2 between each through opening 200*i*, 210*i* in said second row of through openings 20 and said outer edge 3 is to be measured between an edge point 28'''' of the through opening 200*i*, 210*i* closest to the outer edge 3 of the backing layer 2. In this case there are two points, edge points 28'''' and each edge point 28'''' is arranged at a distance D2 from said outer edge 3 and at the circular through holes 210*i*.

Figure 3:
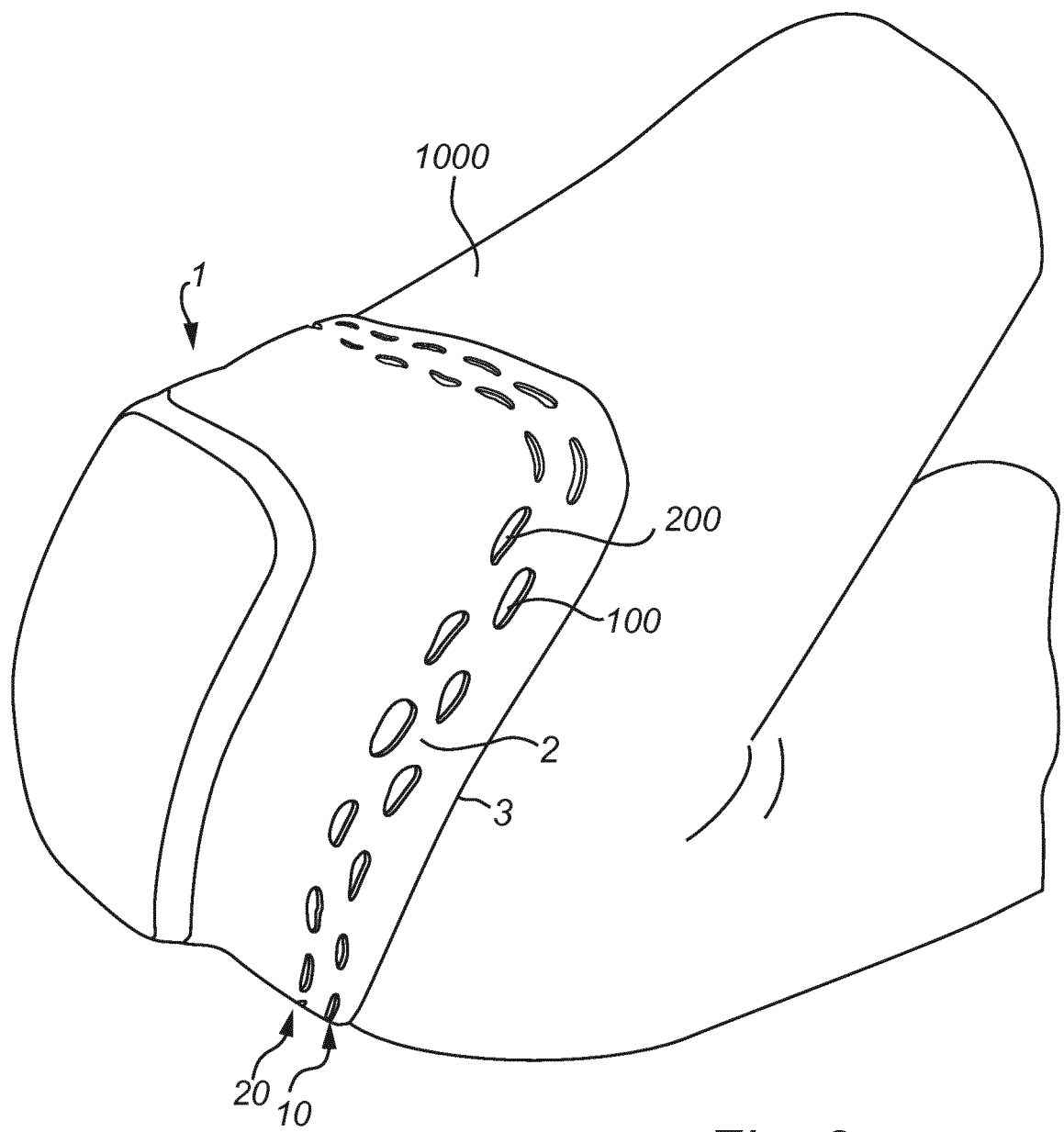
FIG. 3 shows the self-adhesive member in FIG. 1a in use.

FIG. 3 shows the self-adhesive member 1 in FIG. 1 in use attached to a knee 1000 when the knee is being bent. When applying the self-adhesive member 1 to the knee joint 1000 the knee is usually not bent. The self-adhesive member 1 will at this stage get a concave shape over the knee joint and it is held in place with aid of the adhesive of the backing portion. The outer edges 3 of the self-adhesive member 1, which are arranged on either side of the knee 1000, will run substantially parallel to each other. When bending the knee the backing layer 2 between the through openings 100, 200 in the first and the second row of through openings 10, 20, at the side of the knee will stretch when the skin it is attached to is stretched during the bending. By this, stress is induced to the self-adhesive member 1. The through openings 100, 200 in the first and the second rows of through openings 10, 20 will consequently deform by expansion and thereby relax the stress that is induced to the self-adhesive member.

Figure 4:
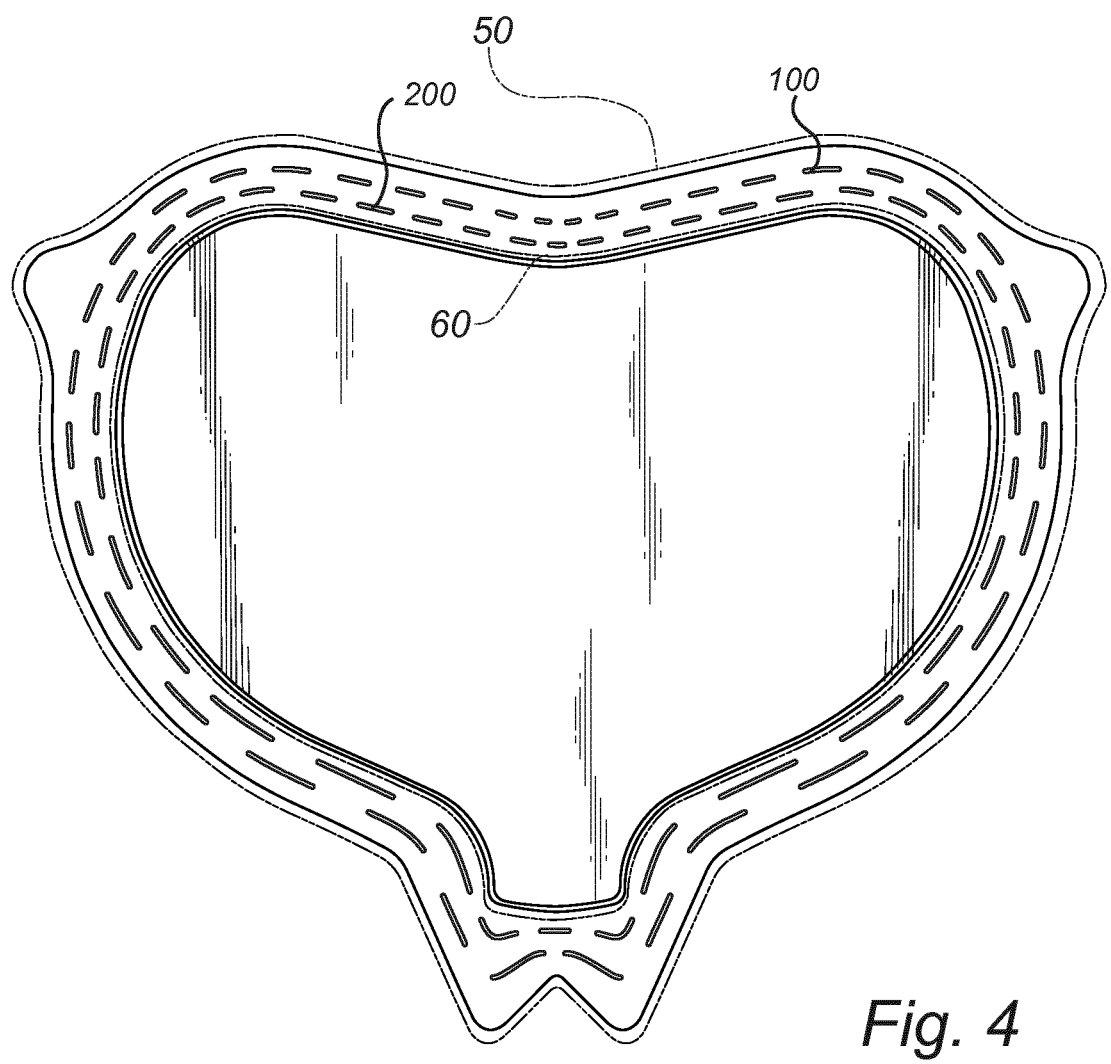
FIG. 4 discloses a self-adhesive member according to a further embodiment of the present invention.

In the embodiment illustrated in FIG. 4, the through openings of the first and second rows are provided in the first portion 50 of the self-adhesive member and may have the size, shape, position and relationship to the other through openings as described above for any one of the previous embodiments. However, the through openings of the first and second row 100, 200 each have a gradually increasing length, as seen from the top of the drawing towards the bottom of the drawing. The embodiment in FIG. 4 illustrates an example embodiment with varying length of the through openings and length between the through openings. However, the varying lengths of the through openings and distances between them may also vary in other ways. It is for example conceivable with embodiments in which the first row and the second row vary independently of each other, or where one of the rows has a constant size of through openings while the through openings of the other row vary along its extension.

The invention has mainly been described above with reference to a few embodiments. However, as is readily appreciated by a person skilled in the art, other embodiments than the ones disclosed above are equally possible within the scope of the invention, as defined by the appended patent claims.

It is for example possible to combine the different embodiments illustrated herein, such that e.g. the embodiments disclosed as being substantially parallel to the edge 3, i.e. the embodiments of FIGS. 2a-2d and 2g-2i may instead be arranged with an angle such as disclosed in FIGS. 2e and 2f to the edge 3.

The invention claimed is:

1. A self-adhesive member for adhering to and covering a portion of a user's skin, said self-adhesive member comprising a backing layer having a self-adhesive coating,
   wherein said backing layer is a polymer film that comprises at least a first and a second portion,
   wherein said first portion surrounds said second portion,
   wherein said first portion comprises at least a first row of slits configured to deform or expand when said self-adhesive member is subjected to a force, said first row of slits extending longitudinally along and parallel to each outer edge of said backing layer thereby extending around a periphery of said self-adhesive member to surround said second portion and being distanced a substantially uniform first distance from each outer edge of said backing layer and wherein said second portion is void of slits,
   wherein said self-adhesive member has a surface area,
   wherein each slit in said first row of slits has an elongated shape, and wherein at least 80 percent of the slits in said first row of slits have a major longitudinal extension aligned in a direction that is the same as a direction of extension of the outer edge of said backing layer that each slit is positioned closest to,
   wherein said backing layer:
   a. only has a single row of slits in said first portion being said first row of slits, or
   b. comprises at least two rows of slits in said first portion, wherein the at least two rows of slits comprise said first row of slits and a second row of slits, wherein said second row of slits extends in a direction along said first row of slits, and
   wherein said self-adhesive member further comprises a wound pad attached to said backing layer at a central area of said self adhesive member such that said wound pad is positioned only in said second portion of said backing layer and is configured to be positioned over a wound during use.

2. The self-adhesive member according to claim 1, wherein said second row of slits is distanced from each outer edge of said backing layer with a second distance, which second distance is greater than said first distance between said first row of slits and each outer edge.

3. The self-adhesive member according to claim 2, wherein each of said slits of said second row of slits has a centre, wherein said slits of said second row of slits and said first row of slits are arranged offset relative to one another such that the centre of substantially all slits of said second row of slits are arranged intermediate of two proximal slits of said first row of slits.

4. The self-adhesive member according to claim 3, wherein said slits in said second row of slits, which have centres arranged intermediate of two proximal slits of said first row of slits, each has a longitudinal extension which is at least as long as a distance (L) between said two proximal slits of said first row of slits.

5. The self-adhesive member according to claim 2, wherein the slits in said second row of slits are distanced a substantially uniform second distance from each outer edge of said backing layer.

6. The self-adhesive member according to claim 1, wherein said first portion constitutes 10-75 percent of the surface area of said self-adhesive member.

7. The self-adhesive member according to claim 1, wherein said substantially uniform first distance is between 2 mm and 10 mm.

8. The self-adhesive member according to claim 1, wherein said first portion of said backing layer further comprises a second row of slits extending in a direction along said first row of slits and said slits in said second row of slits are distanced a uniformly spaced third distance to each proximal slit in said first row of slits.

9. The self-adhesive member according to claim 1, wherein each of said slits in said first and/or second row of slits has a length which is between 2 mm and 10 mm.

10. The self-adhesive member according to claim 1, wherein said slits within said first row of slits and/or said slits within said second row of slits are arranged at a distance from each other which preferably is between 2 mm and 10 mm.

11. The self-adhesive member according to claim 1, wherein said slits in said first row of slits have an elongated shape, and wherein at least 95 percent of the slits have a major longitudinal extension in a direction that is the same as an extension of the outer edge of said backing layer that each slit is positioned closest to.

12. The self-adhesive member according to claim 1, wherein the backing layer only has a single row of slits in the first portion being the first row of slits.

13. The self-adhesive member according to claim 1, wherein the backing layer only has two rows of slits in the first portion.

* * * * *